United States Patent [19]
Inbe et al.

[11] Patent Number: 5,993,401
[45] Date of Patent: Nov. 30, 1999

[54] RELAX INDUCING DEVICE WITH HEARTBEAT DETECTION UNIT

[75] Inventors: Hiroyuki Inbe, Osaka; Akihiro Michimori, Neyagawa; Kusuo Iwanaga, Osaka; Kazumi Ookawa; Satoru Makita, both of Hikone, all of Japan

[73] Assignee: Matsushita Electric Works, Ltd., Kadoma, Japan

[21] Appl. No.: 08/894,522

[22] PCT Filed: Dec. 24, 1996

[86] PCT No.: PCT/JP96/03768

§ 371 Date: Aug. 21, 1997

§ 102(e) Date: Aug. 21, 1997

[87] PCT Pub. No.: WO97/23254

PCT Pub. Date: Mar. 7, 1997

[30] Foreign Application Priority Data

Dec. 25, 1995 [JP] Japan .................................. 7-337246
Jan. 16, 1996 [JP] Japan .................................. 8-005257

[51] Int. Cl.⁶ .............................. A61H 1/00; A61H 23/00

[52] U.S. Cl. .............................. 601/46; 601/49; 601/84; 607/17

[58] Field of Search .................................. 601/49, 46, 84, 601/86, 90, 98, 115, 56, 51, 52, 57, 59, 60, 70; 607/17, 19; 482/900, 9, 54

[56] References Cited

U.S. PATENT DOCUMENTS 5,304,112  4/1994  Mrklas et al. ............................. 600/27

FOREIGN PATENT DOCUMENTS

| 0 028 209 | 6/1981 | European Pat. Off. . |
| 63-300772 | 12/1988 | Japan . |
| 1-131648 | 5/1989 | Japan . |
| 3-272745 | 12/1991 | Japan . |
| 5-42129 | 2/1993 | Japan . |
| 6-209 | 1/1994 | Japan . |
| 7-275363 | 10/1995 | Japan . |
| 1102-598-A | 7/1984 | United Kingdom ...................... 482/54 |
| 1163-853-A | 6/1985 | United Kingdom ...................... 601/46 |
| 3533 597-A | 4/1987 | United Kingdom ...................... 607/17 |

*Primary Examiner*—Danton D. DeMille
*Attorney, Agent, or Firm*—Armstrong, Westerman, Hattori, McLeland & Naughton

[57] ABSTRACT

A relax inducing device comprises a biological parameter detecting unit for detecting biological parameter of a user, stimulus loading unit for providing a stimulus to the user, relax-level determining unit for determining a relax level of the user by comparing the biological parameter provided from the biological parameter detecting unit with at least one relax-level threshold value, and a stimulus control unit for controlling an amount of the stimulus according to the relax level to induce the user into a relax state. In this device, since an optimum amount of stimulus is provided to the user on a real-time basis, it is possible to efficiently and smoothly induce the user into the relax state.

19 Claims, 14 Drawing Sheets

RELAX INDUCING DEVICE WITH HEARTBEAT DETECTION UNIT

BACKGROUND OF THE INVENTION

1. Field of the Invention

The present invention relates to a relax inducing device for inducing a user to a relax state, and particularly a relax inducing device capable of detecting a biological signal of the user such as heartbeat number or respiration number, and controlling an amount of stimulus to be applied to the user according to the biological signal.

2. Disclosure of the Prior Art

In the past, it has been proposed to determine a relax level of a user according to a biological signal such as brain wave or heart rate. For example, Japanese Patent Early Publication [KOKAI] No. 1-131648 discloses to treat values of heartbeat R—R interval defined as a basic period of an electrocardiogram of a user by a high-speed Fourier transform, and determine a relax level index of the user according to a power value of a particular frequency range and a total power value. In addition, Japanese Patent Early Publication [KOKAI] No. 3-272745 discloses to determine an index by calculating a dispersion of the heartbeat R—R interval. Moreover, Japanese Patent Early Publication [KOKAI] No. 5-42129 discloses to detect a respiration signal in addition to a heartbeat signal of a user, and determine a relax level index by calculating a dispersion of at least one of those signals. However, when the dispersion is used as the relax level index, there is a problem that the confidence of the relax level is poor because of individual variations of the users.

As to a relax inducing device such as a massager of providing a stimulus to a user to induce the user into a relax state, it has been known that there are massagers in which a massage motion must be manually adjusted by the user, and a programmed massage motion is provided to the user. In the former massager, there is a problem that the adjusting of the massage motion is troublesome. On the other hand, since the later massager provides the programmed massage motion irrespective of a physical condition of the user, there is a possibility that the user often feels the programmed massage motion uncomfortable.

Thus, there is room for further improvement in the method of determining the relax level index and the relax inducing device.

SUMMARY OF THE INVENTION

For improving the above problems, the present invention is directed to a relax inducing device capable of controlling an amount of stimulus to be applied to a user according to a biological parameter of the user changing moment by moment to induce the user into a relax state. That is, the relax inducing device of the present invention comprises a biological-information detecting unit for detecting at least one biological parameter selected from heartbeat number, respiration number, and brain wave of a user, a stimulus loading unit for providing a stimulus to the user, and a stimulus control unit for controlling an amount of the stimulus according to the detected biological parameter to induced the user into a relax state. The biological-information detecting unit detects the biological parameter of the user when the user utilizes the relax inducing device. The stimulus amount is determined according to the detected biological parameter and provided to the user on a real-time basis. Therefore, it is possible to efficiently and smoothly induce the user into the relax state.

It is preferred that the relax inducing device of the present invention comprises a relax-level determining unit. The relax-level determining unit compares the biological parameter provided from the biological-information detecting unit with at least one relax-level threshold value to determine a relax level of the user. In this case, the stimulus control unit controls the stimulus amount according to the relax level.

In addition, it is preferred that the stimulus control unit controls the stimulus amount such that as the biological parameter is smaller, the stimulus amount decreases.

These and still other objects and advantages will become apparent from the following description of the preferred embodiments of the invention when taken in conjunction with the attached drawings.

PREFERRED EMBODIMENTS OF THE INVENTION

Figure 1:
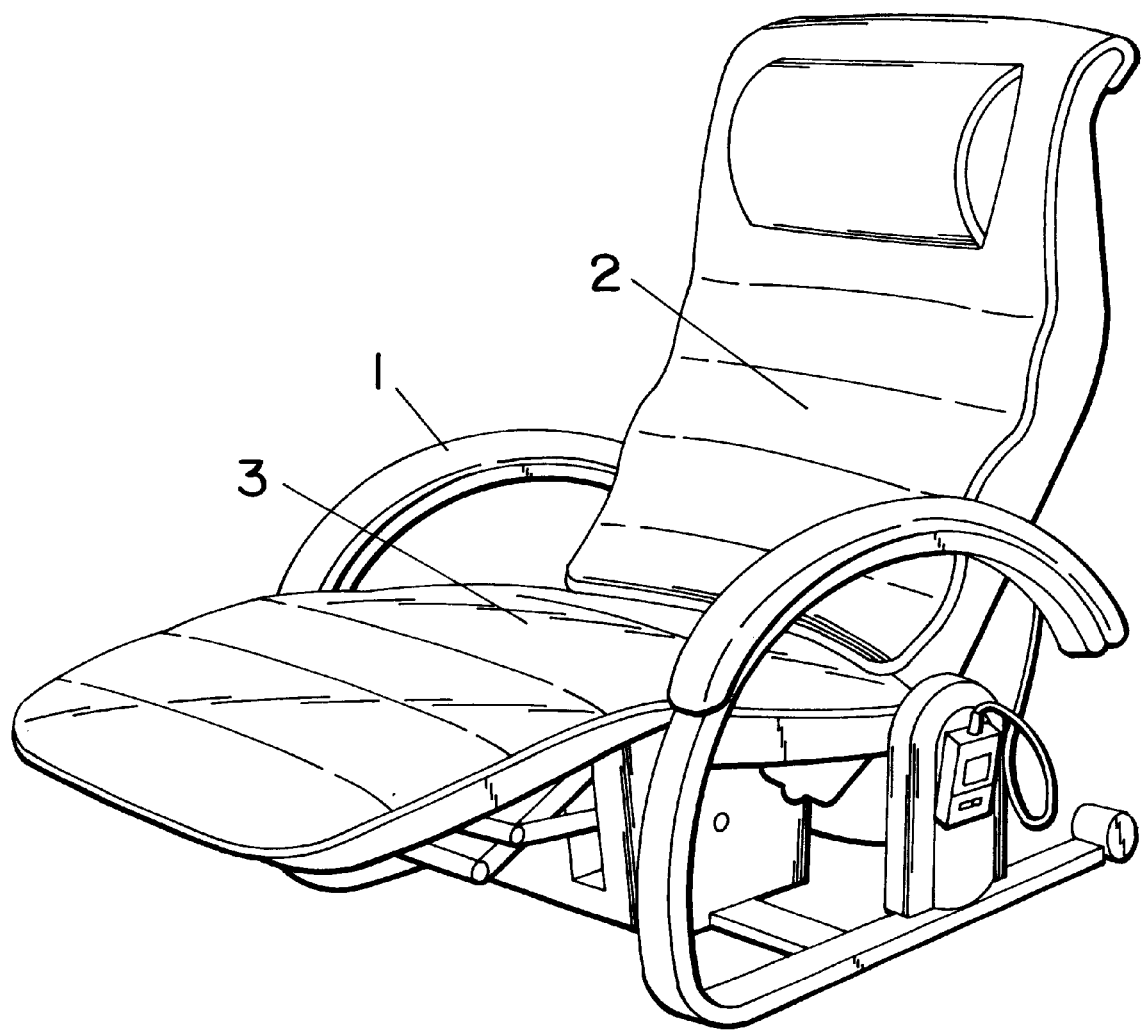
FIG. 1 is a perspective view of a massage chair, which is an embodiment of a relax inducing device of the present invention.
Figure 2:
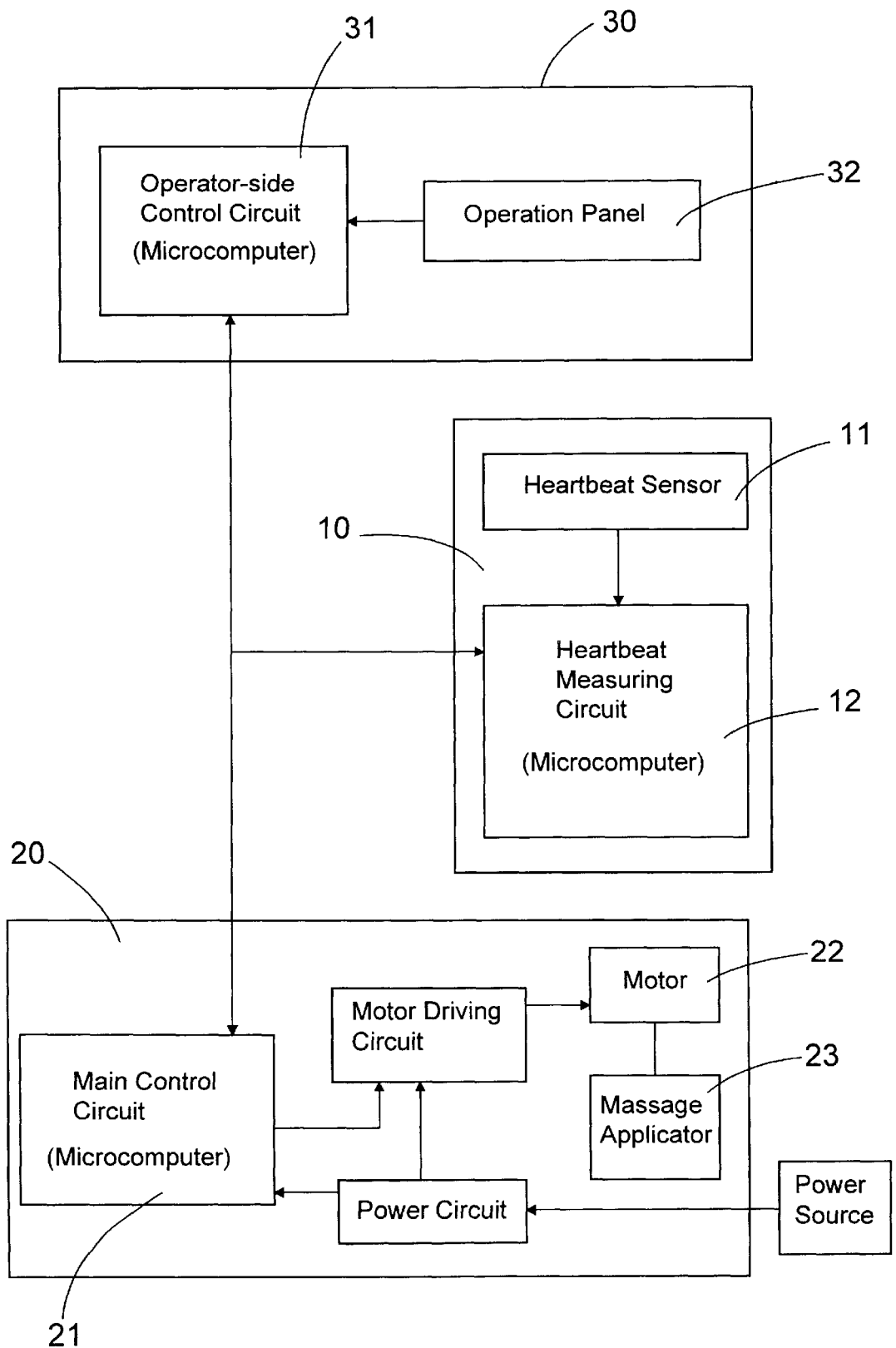
FIG. 2 is a schematic control diagram of the massage chair of FIG. 1.

The present invention is explained in detail referring to the attached drawings. FIG. 1 shows a massage chair 1 as an embodiment of a relax inducing device of the present invention. As shown in FIG. 2, this massage chair 1 comprises a heartbeat-number detecting unit 10 for detecting heartbeats of a user, a massage applicator 23 of applying a massage stimulus to the user, a massage control unit 20 including a microcomputer for controlling an action of the massage applicator according to the heartbeat information provided from the detecting unit 10, and a massage operation unit 30 which can be operated by the user.

The heartbeat-number detecting unit 10 is provided with a heartbeat sensor 11 and a heartbeat measuring circuit 12 of a microcomputer. As the heartbeat sensor 11, it is possible to use a restriction-type sensor which is directly loaded to a user to detect heartbeats. However, to smoothly inducing the user into a relax state without a sensation of pressure, it is preferred to use a non-restriction type sensor capable of detecting the heartbeats without being directly loaded to the user. As the non-restriction type sensor, it is possible to use a piezoelectric element or a capacitance-type sensor which may be arranged on a plane of the massage chair for supporting a weight of the user, or an optical fiber which is connected at its opposite ends to a light projecting element and a light receiving element. In the massage chair of FIG. 1, the heartbeat number detecting unit 10 is disposed inside a seat cushion 3 of the massage chair, so that heartbeats of the user sitting on the massage chair 1 can be readily measured by the heartbeat sensor 11. The massage operating unit 30 is provided with an operator-side control circuit 31 of a microcomputer and an operation panel 32 available to the user.

The massage control unit 20 is incorporated in a backrest 2 of the massage chair 1. The massage applicator 23 is driven by a motor 22. Various factors for operating the massage applicator 23 can be determined through the operation panel 32. In the massage chair 1 of this embodiment, it is possible to select one massage mode from various massage operations of a "pushing-up massage" mode, "pushing-down massage" mode, "tapping massage" mode, "rubbing massage mode for straightening back", "rubbing massage mode for partially straightening back", "complex massage mode for straightening back while tapping", and "complex massage mode for partially straightening back while tapping". As to details of these massage operations, conventional techniques already known in this art can be used.

A main control circuit 21 of a microcomputer included in the massage control unit 20 of the massage chair 1 carries out an auto massage mode when a user selects a "relax" course by pushing a button for the auto massage mode of the operation panel 32. In the auto massage mode, a massage action of the applicator 23 is controlled according to the heartbeat information of the user output from the heartbeat-number detecting unit 10. Referring to FIGS. 3 to 6, a control pattern of a massage speed of the present invention is explained in detail. After the control circuit 21 receives a signal indicative of the selection of the "relax" course from the operation panel 32, the massage mode for straightening back and the massage mode for straightening back while tapping are carried out for predetermined time periods, respectively. The massage action of the applicator 23 comes to a halt, and then an initial massage mode is started. In this explanation, the initial massage mode is performed for 20 seconds at a massage speed of 14 times/min to determine an initial heartbeat value HR(0). The initial heartbeat value HR(0) is used as a standard value for determining a relax level of the user, and compared with a heartbeat value HR(n) subsequently measured by the heartbeat-number detecting unit 10. In this case, the massage speed is classified into six grades according to the relax level. That is, when ΔHR, which is presented by the following equation:

$$\Delta HR = \{(HR(0) - HR(n))/HR(0)\} \times 100,$$

is within a range of 0% to less than 2% (1st stage), the massage applicator 23 is driven at a first massage speed S1 (defined as an action number (times) of the massage applicator per minute), e.g., 24 times/minute. When ΔHR is within a range of 2% to less than 4% (2nd stage), the applicator is driven at a second massage speed S2 slower than the first massage speed, e.g., 22 times/minute. When ΔHR is within a range of 4% to less than 8% (3rd stage), the applicator is driven at a third massage speed S3 slower than the second massage speed, e.g., 20 times/minute. When ΔHR is within a range of 8% to less than 11% (4th stage), the applicator is driven at a fourth massage speed S4 slower than the third massage speed, e.g., 18 times/minute. When ΔHR is within a range of 11% to less than 13% (5th stage), the applicator is driven at a fifth massage speed S5 slower than the second massage speed, e.g., 16 times/minute. When ΔHR is within a range of 13% or more (6th stage), the massage action of the applicator is stopped.

In each of the 1st to 5th stages, the massage is applied to the user at the respective massage speed for at least minimum time period. In this embodiment, the minimum time period is set to 30 seconds in each of the stages. In addition, a maximum time period of massage is set to 55 seconds in each of the stages. For example, when ΔHR reaches the range of 2% to less than 4% during the massage action of the applicator at the first massage speed for 30 to 55 seconds, the first massage speed is changed to the second massage speed. By the way, when ΔHR does not substantially change for a predetermined time period (a predetermined action number (times) of the massage applicator) during the massage action, it is preferred to slow down the present massage speed to a one-stage slower massage speed. In this embodiment, when ΔHR does not substantially change for 55 seconds of the maximum time period, the present massage speed is automatically reduced to the one-stage slower massage speed. In addition, when ΔHR does not reach the range of 13% or more even after 55 seconds pass from a beginning of the massage action at the fifth massage speed S5, the massage action is automatically stopped. Therefore, it is possible to efficiently induce the user to the relax state without interrupting the relax state such as a dozing state of the user. As to the control pattern of this embodiment, a minimum time period for inducing the user to the relax state, which includes the time period for the initial massage mode, is 2 minutes and 50 seconds, as shown by the line PS of FIG. 3. On the other hand, a maximum time period for inducing the user to the relax state, which includes the time period for the initial massage mode, is 4 minutes and 55 seconds, as shown by the line PL of FIG. 3. As a result, the 6-stage control of the massage speed can be performed within a range surrounded with the control patterns PS and PL. Although a time period necessary for inducing the user to the relax state changes in response to health and mental conditions of the user, it is normally about 3 minutes and 30 seconds.

Figure 3:
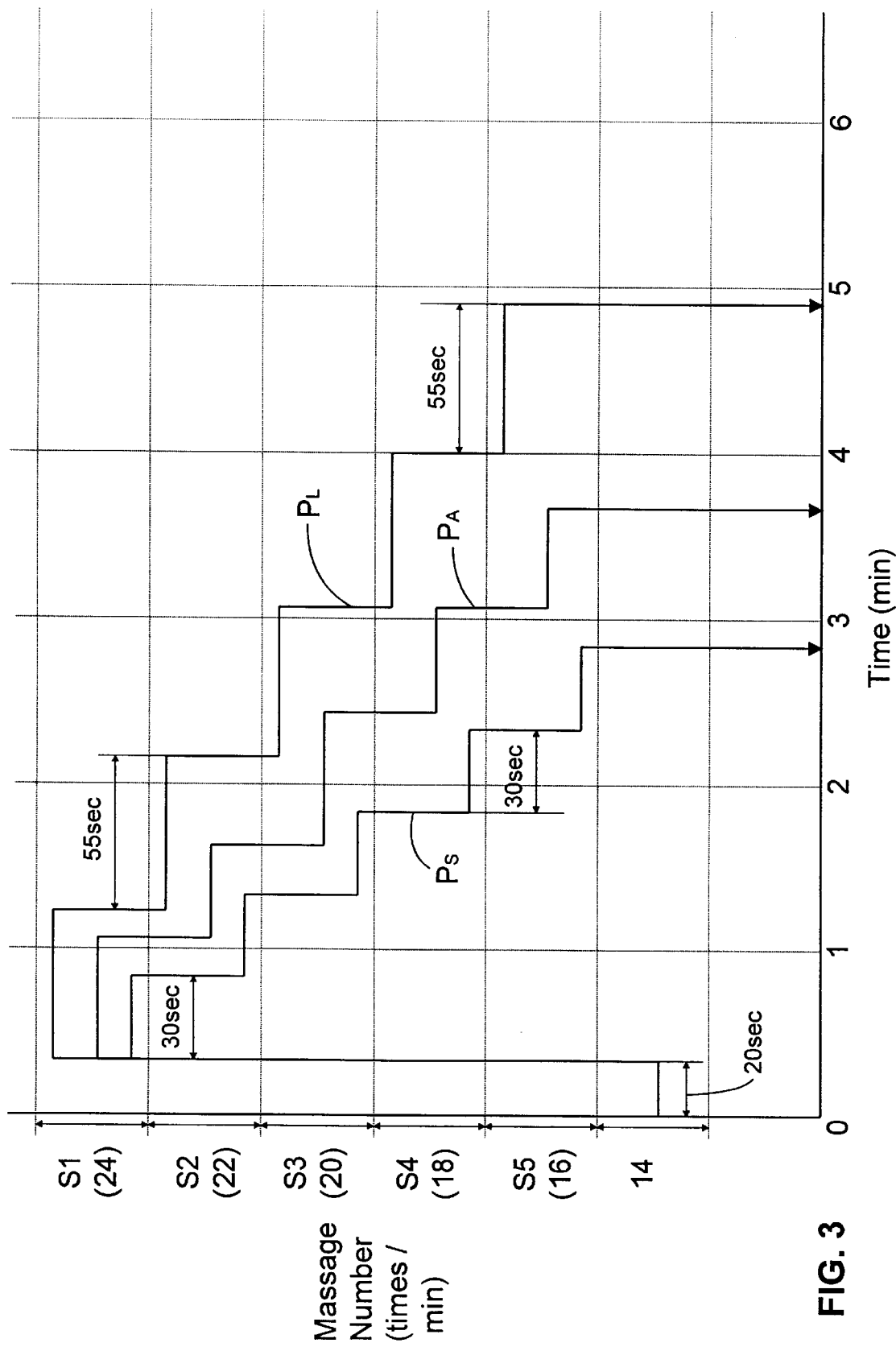
FIG. 3 is a graph explaining a control of a massage speed of a massage applicator in an auto-massage mode of the present massage chair.

As an example, a user A was induced to a relax state along a massage speed control pattern shown by the line PA of FIG. 3 by the use of the above massage chair 1. That is, the user A firstly received the initial massage for 20 seconds at the massage speed of 14 times/min to obtain an initial heartbeat value HR(0). Subsequently, a massage was started at the first massage speed of 24 times/min. ΔHR reached within the range of 2 to less than 4% just after the elapse of 45 seconds from the beginning of the massage action at the first massage speed, so that the first massage speed was changed to the second massage speed. ΔHR reached within the range of 4 to less than 8% just after the elapse of 35 seconds from the beginning of the massage action at the second massage speed, so that the second massage speed was changed to the third massage speed. ΔHR reached within the range of 8 to less than 11% just after the elapse of 50 seconds from the beginning of the massage action at the third massage speed, so that the third massage speed was changed to the fourth massage speed. In addition, ΔHR reached within the range of 11 to less than 13% just after the elapse of 35 seconds from the beginning of the massage action at the fourth massage speed, so that the fourth massage speed was changed to the fifth massage speed. Finally, ΔHR reached the range of 13% or more just after the elapse of 35 seconds from the beginning of the massage action at the fifth massage speed, the massage action was stopped. At this time, it was confirmed that the user A reached a sleeping state which is one of relax states. In this example, a time period necessary for inducing the user A to the relax state is about 3 minutes and 40 seconds. This total time period includes the time period for the initial massage.

Figure 4:
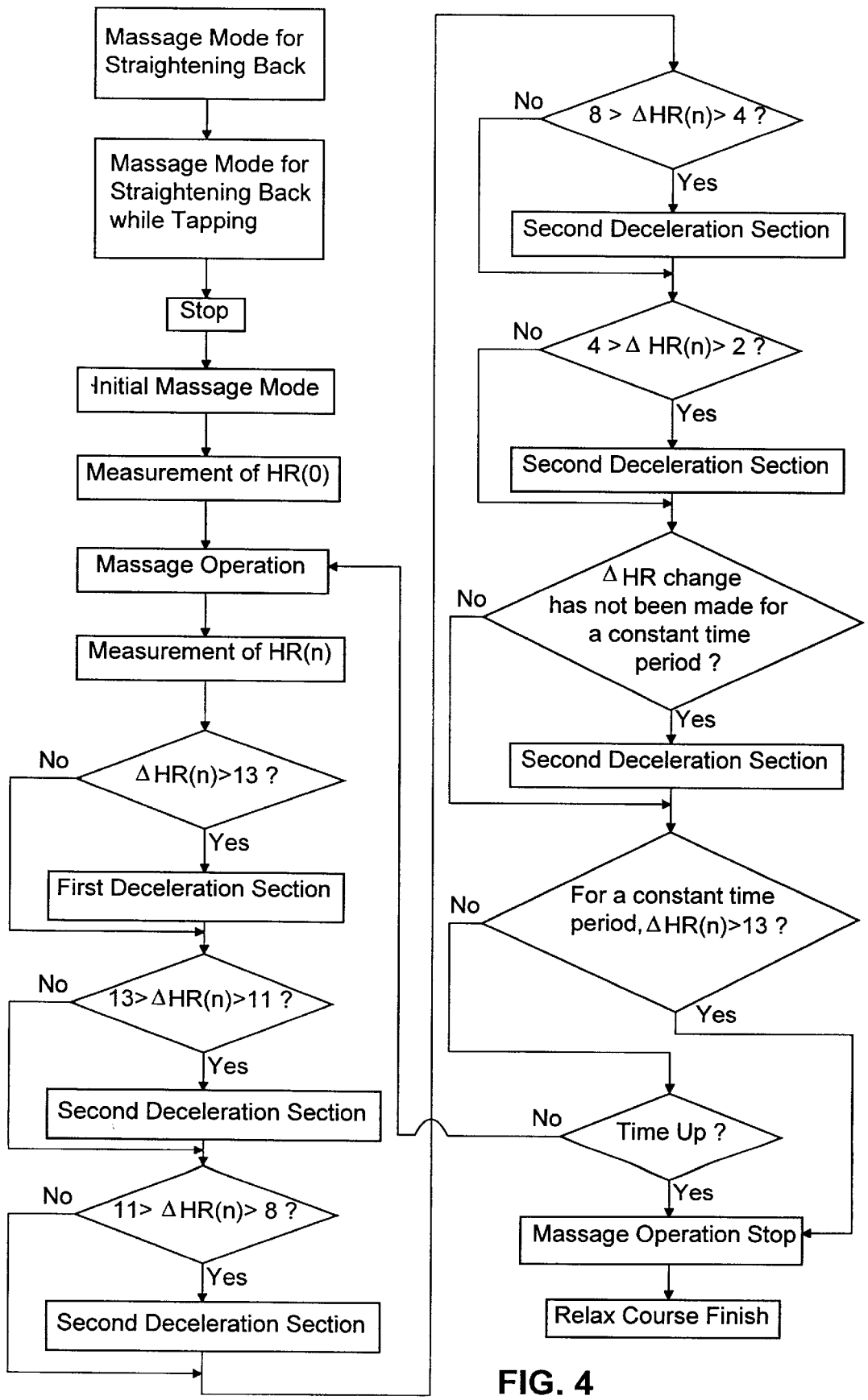
FIG. 4 is a flow chart of the auto massage mode of the massage chair.
Figure 5A:
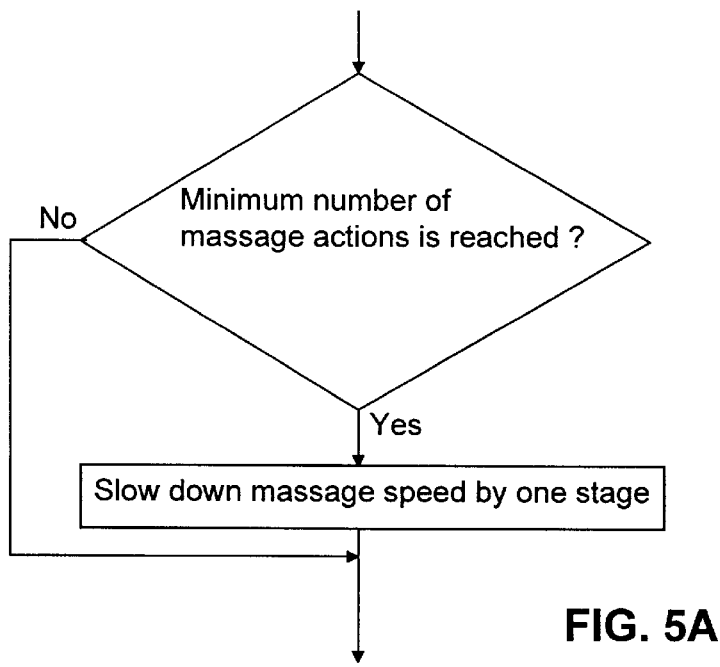
FIGS. 5A and 5B are detail flow charts of first and second deceleration sections of FIG. 4, respectively.
Figure 5B:
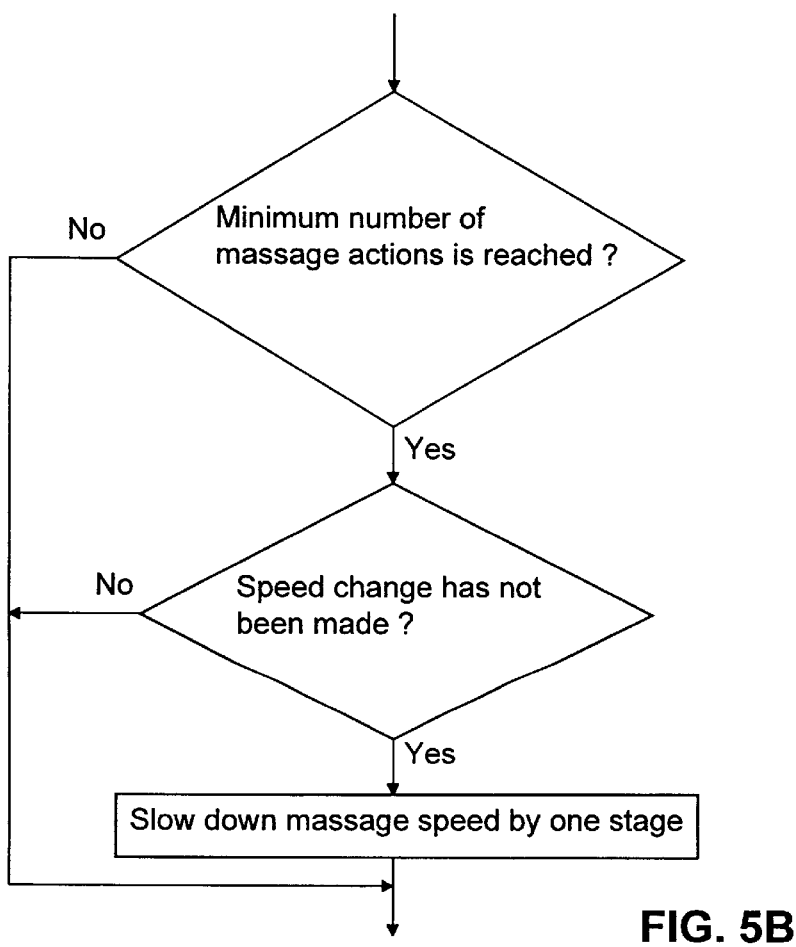

Thus, it is preferred to use relax-level threshold values of 0, 2, 4, 8, 11, and 13% to provide the 6-stage control of the massage speed of the applicator. However, needless to say, it is possible to select another relax-level threshold values. By the way, when the heartbeat number increases during a massage stage, it is preferred to keep a massage speed of the massage stage to smoothly induce the user to the relax level. In addition, if necessary, a massage action having a sixth massage speed (S6≠0) may be given to the user when ΔHR reaches the range of 13% or more. In this case, the massage action of the sixth massage speed may be stopped after being carried out for a predetermined time period. In FIG. 4, a flow chart of the automatic massage mode of the present massage chair 1 is shown. In addition, FIGS. 5A and 5B show detail flow charts of first and second deceleration sections shown in the flow chart of FIG. 4, respectively.

Figure 6:
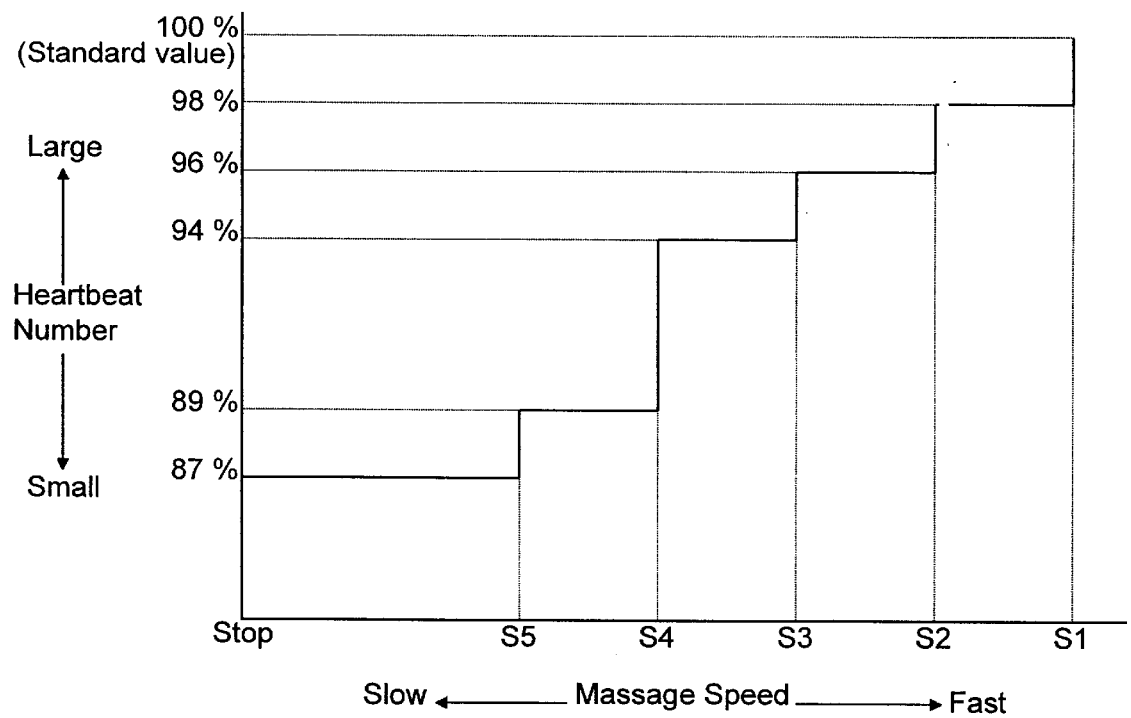
FIG. 6 is a graph showing a relationship between massage speed of the applicator and heartbeat number in a six-stage control.
Figure 7:
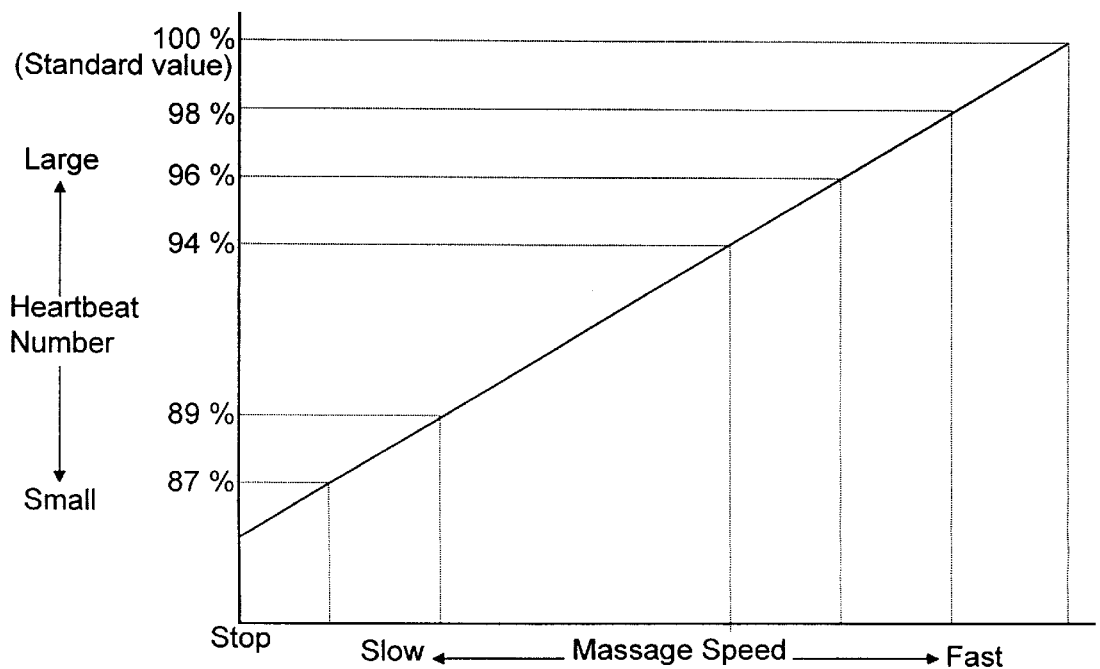
FIG. 7 is a graph showing a relationship between massage speed of the applicator and heartbeat number in an infinite-stage control.

As shown in FIG. 6, the massage speed of the massage chair 1 of this embodiment is classified into 6 grades. Alternatively, it is possible to use a massage control system with infinitely variable speeds, as shown in FIG. 7. The number of control stages of the massage speed is not limited to the above, although, it is preferred to classify the massage speed into at least 3 stages. For example, in case of selecting the 3 stages, it is preferred to select two relax-level threshold values from a range of 0 to less than 8% and a range of 8 to 16%, respectively.

The massage chair 1 of this embodiment uses the heartbeat-number detecting unit 10. Alternatively, a respiration-number detecting unit may be used. When a massage is provided to the user at a massage cycle slightly longer than a detected respiration cycle, the respiration cycle gradually approaches to the massage cycle. As a result, since the respiration cycle moderately elongates, it is possible to smoothly induce the user into the relax state.

Moreover, both of the heartbeat-number detecting unit 10 and the respiration-number detecting unit may be used to the massage chair of the present invention, if necessary. Alternatively, it is possible to use a brain-wave detecting unit. In this case, it is preferred that an occupation ratio of α wave is used as a control factor of the massage speed of the massage applicator. Needless to say, the massage speed can be controlled according to a combination of the brain-wave information and the heartbeat information or a combination of the respiration information and the heartbeat information.

Figure 8:
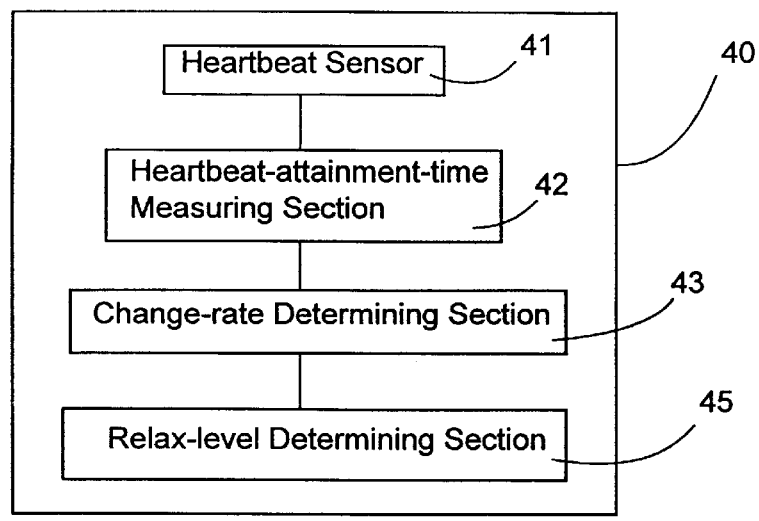
FIG. 8 is a schematic diagram of a relax-level determining unit.

In place of the heartbeat-number detecting unit 10 and the control circuit 21 of the massage chair 1, a relax-level determining unit 40 can be used to control the massage speed of the applicator, as shown in FIG. 8. That is, the relax-level determining unit 40 comprises a heartbeat sensor 41 for sensing heartbeats of the user, a heartbeat-attainment-time measuring section 42 for providing a heartbeat attainment time, which is defined as a time period necessary to reach a predetermined heartbeat number, and measured every cycle of the predetermined heartbeat number, a change-rate determining section 43 for providing a change rate defined as a ratio of an initial heartbeat attainment time measured at an initial cycle of the predetermined heartbeat number to a heartbeat attainment time measured at a subsequent cycle of the predetermined heartbeat number, and a relax-level determining section 45 for determining the relax level of the user by comparing the change rate with at least one of predetermined relax-level threshold values.

The heartbeat sensor used in the massage chair 1 of the FIG. 1 can be used as the heartbeat sensor 41. As an example, when the predetermined heartbeat number is set to 20 times, the heartbeat-attainment-time measuring section 42 successively measures a time period necessary to reach the heartbeat number of 20 times at every cycle of the heartbeat number. In other words, a time period necessary to reach the heartbeat number of 20 times at an initial cycle, a time period necessary to reach the heartbeat member of 20 times at the next cycle, and a time period necessary to reach the heartbeat member of 20 times at the cycle after next, are successively measured by the measuring section 42. A ratio of the time period measured at the initial cycle to the time period measured at each of the subsequent cycles is determined as the change rate of the heartbeat attainment time by the change-rate determining section 43. The relax-level determining section 45 determines the relax level of the user by comparing the change rate output from the change-ratio determining section 43 with the relax-level threshold value. In this case, it is preferred to classify the massage speed of the massage applicator into three stages according to the relax level in order to efficiently induce the user to a relax state. That is, when the change rate is within a range of 0% to less than 4%, a massage speed of the applicator defined as an action number (times) of the applicator per minute is determined to a first massage speed. When the change rate is within a range of 4% to less than 11%, the first massage speed is changed to a second massage speed slower than the first massage speed. When the change rate reaches a range of 11% or more, the second massage speed is changed to a third massage speed slower than the second massage speed. In this relax-level determining section, it is possible to accurately determine the relax level of the user without depending on complex arithmetic operations such as Fourier transform.

Figure 9:
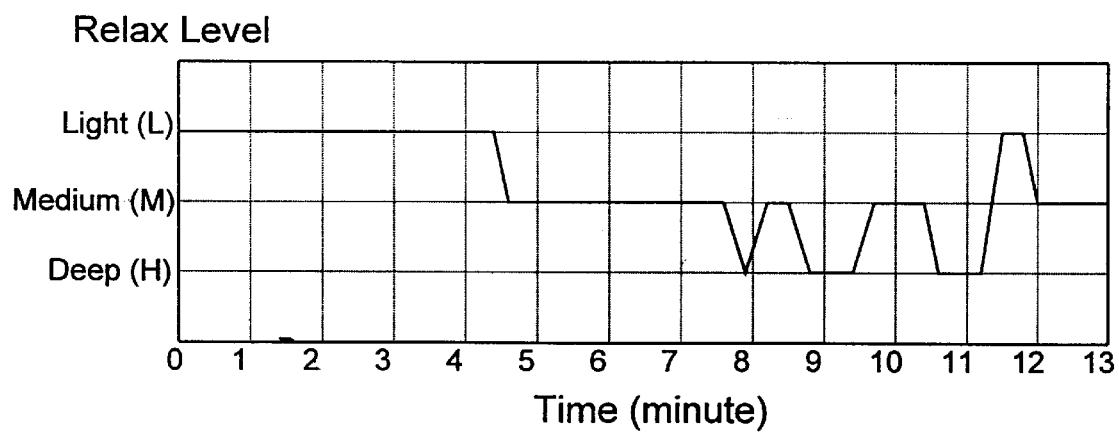
FIG. 9 is a graph showing a change on time of a relax level of a user obtained by a brain-wave measurement
Figure 10:
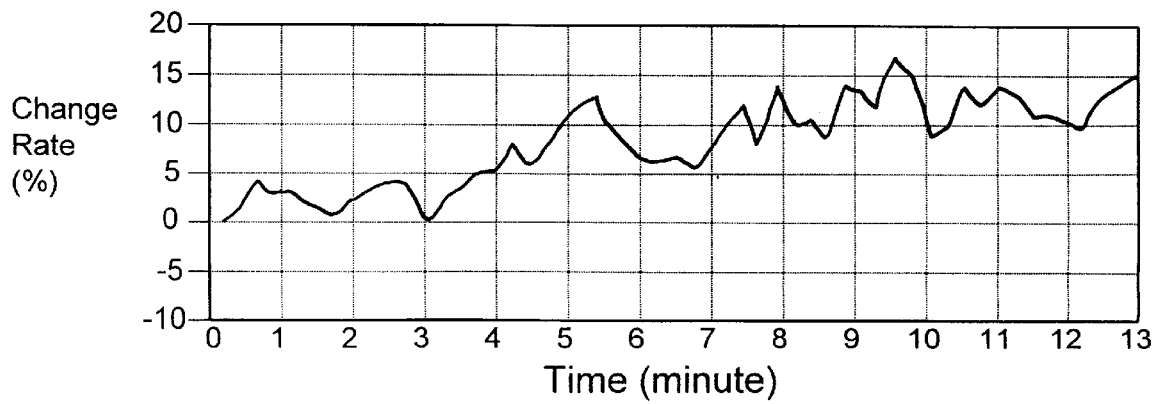
FIG. 10 is a graph showing a change on time of a change rate of a heartbeat attainment time which is defined as a time period necessary to reach a heartbeat number of 20 times.

For the following reasons, it is preferred to use the relax-level threshold values (4% and 11%). That is, a correlation between a relax level of a user derived from a brain-wave measurement and the change rate of the heartbeat attainment time determined according to the heartbeat measurement was investigated. FIG. 9 shows a change on time of the relax level according to results of the brain-wave measurement. On the other hand, FIG. 10 shows a change on time of the change rate of the heartbeat attainment time defined as the time period necessary to reach the heartbeat number of 20 times. An increase of the change rate (%) as time passed means that the time period necessary to reach the heartbeat number (20 times) gradually extends. In other words, this means that the user is gradually approaching the relax state. As to a classification of the relax level of FIG. 9, when more than 50% of the brain wave is α wave and the balance is θ wave, or all of the brain wave is α wave, it defined as a light relax level (L). When more than 50% of the brain wave is θ wave and the balance is α wave, or all of the brain wave is θ wave, it defined as a medium relax level (M). When a special wave called as humps which can be observed at a relax state appears during the measurement, it defined as a deep relax level (H). In FIG. 9, the relax level of the user transferred from the light relax level (L) to the medium relax level (M) after the elapse of about 4 minutes from the beginning of measurement. Subsequently, the relax level of the user also transferred from the medium relax level (M) to the deep relax level (H) after the elapse of about 8 minutes from the beginning of measurement.

Figure 11:
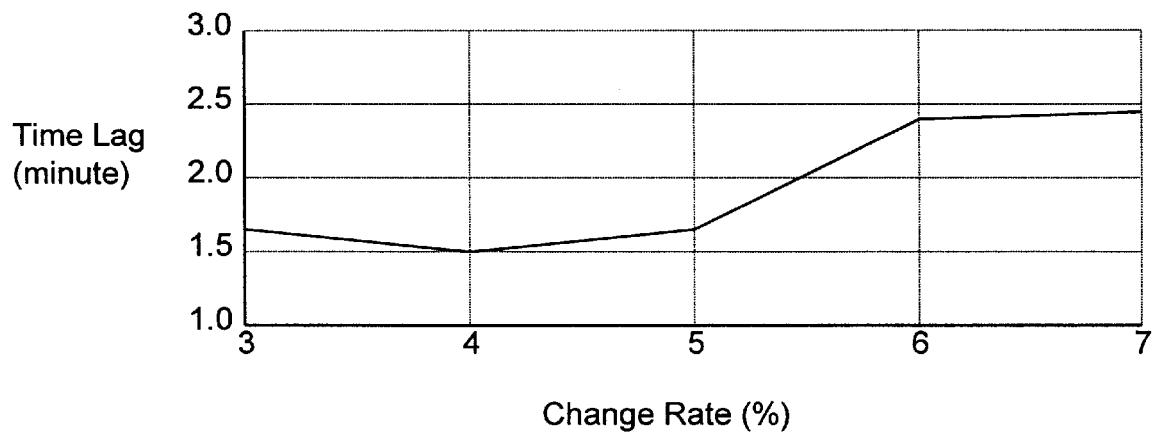
FIG. 11 is a graph showing a time lag (minute) when each of change rates of 3% to 7% is used as a relax-level threshold value.
Figure 12:
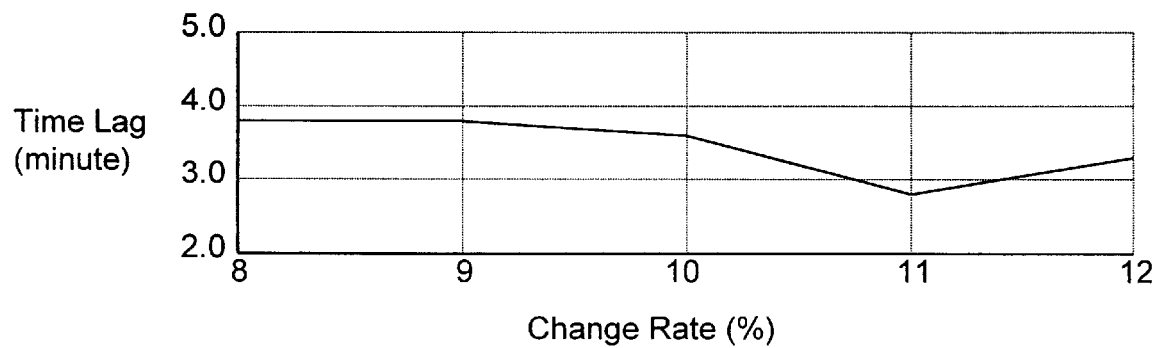
FIG. 12 is a graph showing a time lag (minute) when each of change rates of 8% to 11% is used as a relax-level threshold value.

To determine the relax level according to the change rate of the heartbeat attainment time so as to match with the results of the brainwave measurement, each of the change rates 3, 4, 5, 6, and 7% was supposed as a relax-level threshold value between the light relax level (L) and the medium relax level (M), and an analysis was carried out as to which change rate is suitable for the threshold value. As a result, it was confirmed that a time lag (absolute value) between a timing of transferring from the light relax level (L) to the medium relax level (M) in the brain-wave measurement of FIG. 9 and a timing of transferring from a light relax level (L) to a medium relax level (M) in the heartbeat measurement is the smallest when 4% of the change rate is selected as the threshold value, as shown in FIG. 11. This means that 4% of the change rate is the most preferable to the threshold value between the light relax level (L) and the medium relax level (M). Similarly, each of the change rates 8, 9, 10, 11, 12 and 13% was supposed as a relax-level threshold value between the medium relax level (M) and the deep relax level (H), and an analysis was carried out as to which change rate is suitable for the threshold value. As a result, it was confirmed that a time lag (absolute value) between a timing of transferring from the medium relax level (M) to the deep relax level (H) in the brain-wave measurement and a timing of transferring from a medium relax level (M) to a deep relax level (H) in the heartbeat measurement is the smallest when 11% of the change rate is selected as the threshold value, as shown in FIG. 12. This means that 11% of the change rate is the most preferable to the threshold value between the medium relax level (M) and the deep relax level (H).

Thus, when the relax level of the user is determined from three grades according to the change rate of the time period necessary to reach the heartbeat number, e.g., 20 times, at the initial cycle to the time period necessary to reach the heartbeat number at the subsequent cycle, it is preferred to use 4% and 11% of the change rates as the relax-level threshold values. It should be understood that the change rates (4% and 11%) are suitable for the relax-level threshold values when the heartbeat number in each cycle is set to 20 times, and the change rate is determined on the basis of the time period necessary to reach the heartbeat number (20 times) at the initial cycle. Therefore, the relax-level threshold values are not limited to the above threshold values. In place of the above change rate, it is possible to use a change rate determined on the basis of an average value of a time period necessary to reach a predetermined heartbeat number at an initial cycle and a time period necessary to reach the heartbeat number at the next cycle.

In case of providing a massage stimulus to a user by the use of a massage chair with the relax-level determining unit explained above for determining the relax level from the three grades, for example, it is preferred to smoothly induce the user into a relax state that when the determined relax level is within a light relax level (the change rate is within the range of 0% to less than 4%), an massage action of the applicator is provided to the user at a massage speed of 24 times/min, when the relax level is within a medium relax level (the change rate is within the range of 4% to less than 11%), the massage action is provided at a massage speed of 20 times/min, and also when the relax level is within a deep relax level (the change rate is within the range of 11% or more), the massage action is provided at a massage speed of 16 times/min. Since experimental data show that when the massage action is provided at a massage speed of 26 times/min or more, it is difficult to efficiently induce the user to the relax level, it is preferred to use the massage speed of less than 26 times/min. In addition, it is possible to control an intensity of massage in place of changing the massage speed. In this case, as the relax level is deeper, the massage intensity may be reduced. Alternatively, it is preferred to simultaneously control both of the massage intensity and the massage speed. It is preferred that the massage action is applied to a body portion such as a shoulder or neck to smoothly induce the user into the relax state.

As to the massage chair 1 explained above, since it is characterized in that massage action of the applicator is controlled on a real-time basis according to the heartbeat signal of the user, it is needless to say that an accurate detection of the heartbeat signal presents an massage action adequate for a physical condition of the user. Therefore, it is preferred to use a heartbeat-signal revising unit described below for checking as to whether a noise signal is included in the heartbeat signal, and revising the heartbeat signal when the noise signal is included.

The heartbeat-signal revising unit is provided with a standard-value deriving section, first and second heartbeat-signal revising sections. The standard value deriving section provides a heartbeat-signal standard value which is defined as an average value of heartbeat-signal intervals when heartbeat signals having a dispersion of heartbeat-signal interval within a required percentage continue for more than a predetermined number of times. The first heartbeat-signal revising section cancels a detected heartbeat signal when the detected heartbeat signal appears at a first interval of less than a predetermined percentage of the heartbeat-signal standard value. On the other hand, the second heartbeat-signal revising section provides a supplemental signal when a detected heartbeat signal appears at a second interval of more than a predetermined percentage of the heartbeat-signal standard value. The supplement signal is inserted into the second interval. Concretely, a heartbeat change of a user detected by a heartbeat sensor is converted to electrical signals by a detecting circuit, and further converted into digital signals by a digitizing circuit. Subsequently, the digital signals are input to a microcomputer (CPU). The checking and revising operations of the heartbeat signals are performed in this CPU. In the following explanation, a leading edge of each of the heartbeat signal is regarded as a heartbeat.

Figure 13:
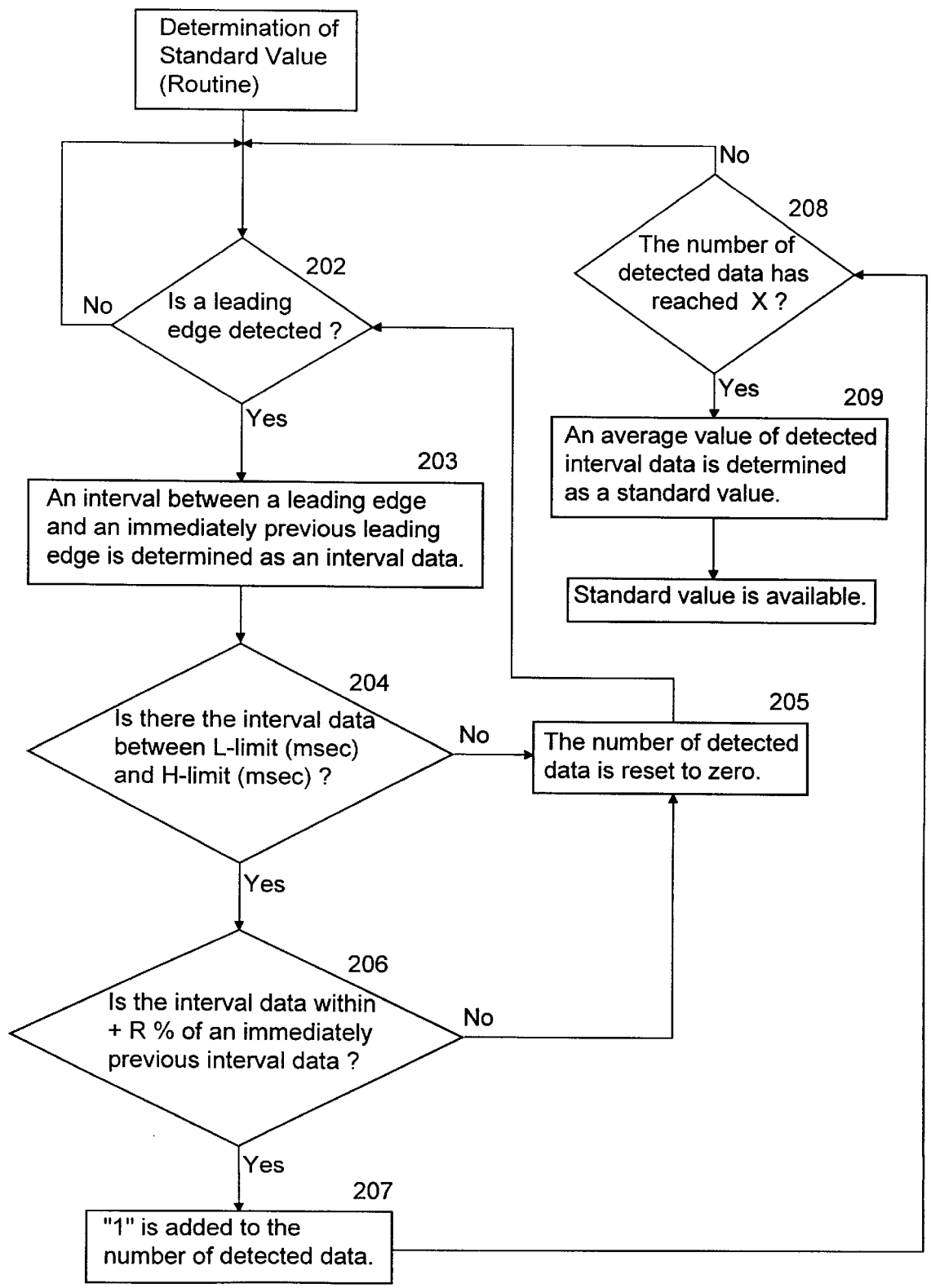
FIG. 13 is a flow chart showing a data treatment in a standard value deriving section.
Figure 14A:
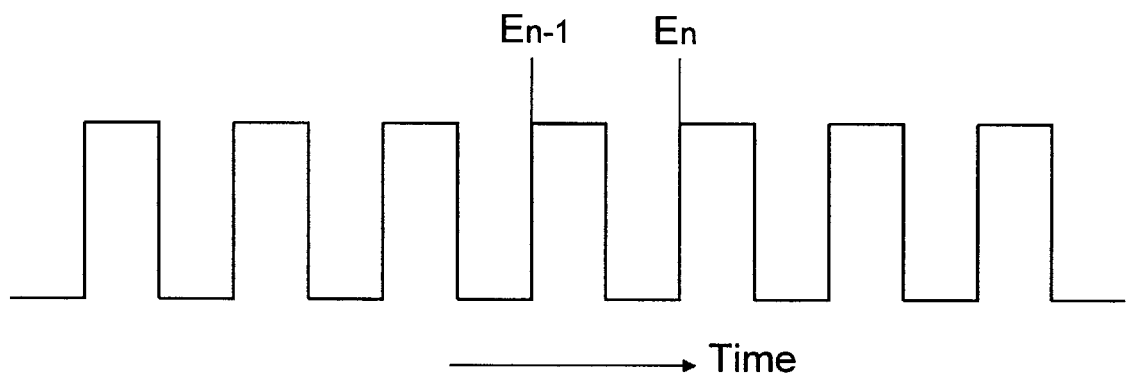
FIG. 14A is a diagram showing leading edges of normal heartbeat signals.

A flow chart of data treatment in the standard value deriving section is shown in FIG. 13. At the step 202, a heartbeat data is detected. At the step 203, an interval between a leading edge (En) of a heartbeat signal and a leading edge (En-1) of an immediately previous heartbeat signal is output as an interval data, as shown in FIG. 14A. At the step 204, a checking operation as to whether the interval data is normal as the heartbeat interval of human is performed. That is, the step 204 is to check as to whether the interval data is in a range between an upper-limit value (H-limit msec) of the heartbeat interval of human and a lower-limit value (L-limit msec) of the heartbeat interval. The upper-limit and lower-limit values can be optionally determined. When the interval data is out of the range, an accumulation number of the heartbeat detection is reset to zero to wait a next interval data. When the interval data is normal, in other words, the interval data is within the range, a checking operation as to whether a dispersion of the interval data is within ±R % of the immediately previous interval data is performed at the step 206. The R value is a threshold value for checking the dispersion, which is determined according to a user and a component of the individual relax inducing device. However, it is preferred to select the R value from a range between 20% and 30%. At the step 206, when the interval date is regarded as unusual, an accumulation number of the heartbeat detection is reset to zero to wait a next interval data. At the step 206, when the interval date is regarded as normal, "1" is added to the accumulation number of the heartbeat detection at the step 207. By repeating the above procedure from the step 202 to the step 207, a predetermined number (n) of successive, normal interval data are stored (step 208). At the step 209, an average value of those normal interval data is determined as the heartbeat-signal standard value. The number (n) of interval data is not limited, however, it is preferred to determine the number (n) of interval data within a range of 3 to 10, and more preferably within a range of 4 to 6, from the viewpoint of massage efficiency and confidence of the relax inducing device. Thus, the heartbeat-signal standard value is determined at the standard value deriving section, and is used at the first and second heartbeat-signal revising sections. This standard value deriving section can provide an accurate heartbeat-signal standard value for a shortened time period.

Figure 14B:
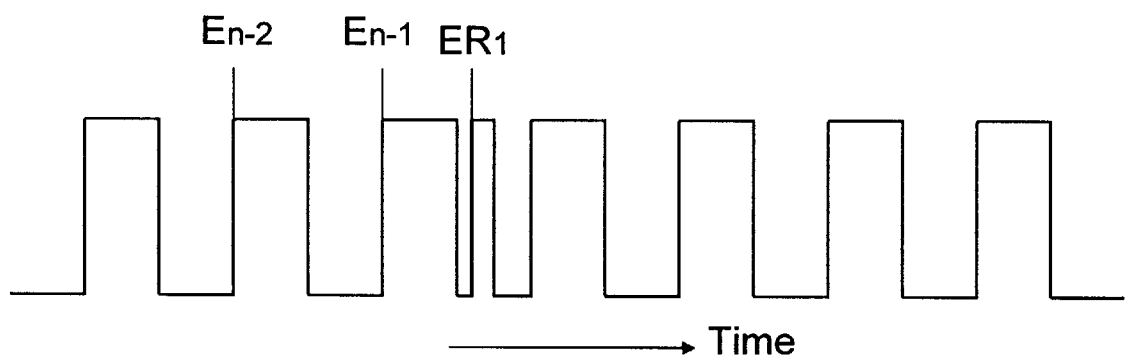
FIG. 14B is a diagram showing heartbeat signals having a noise signal (misinformation)
Figure 15:
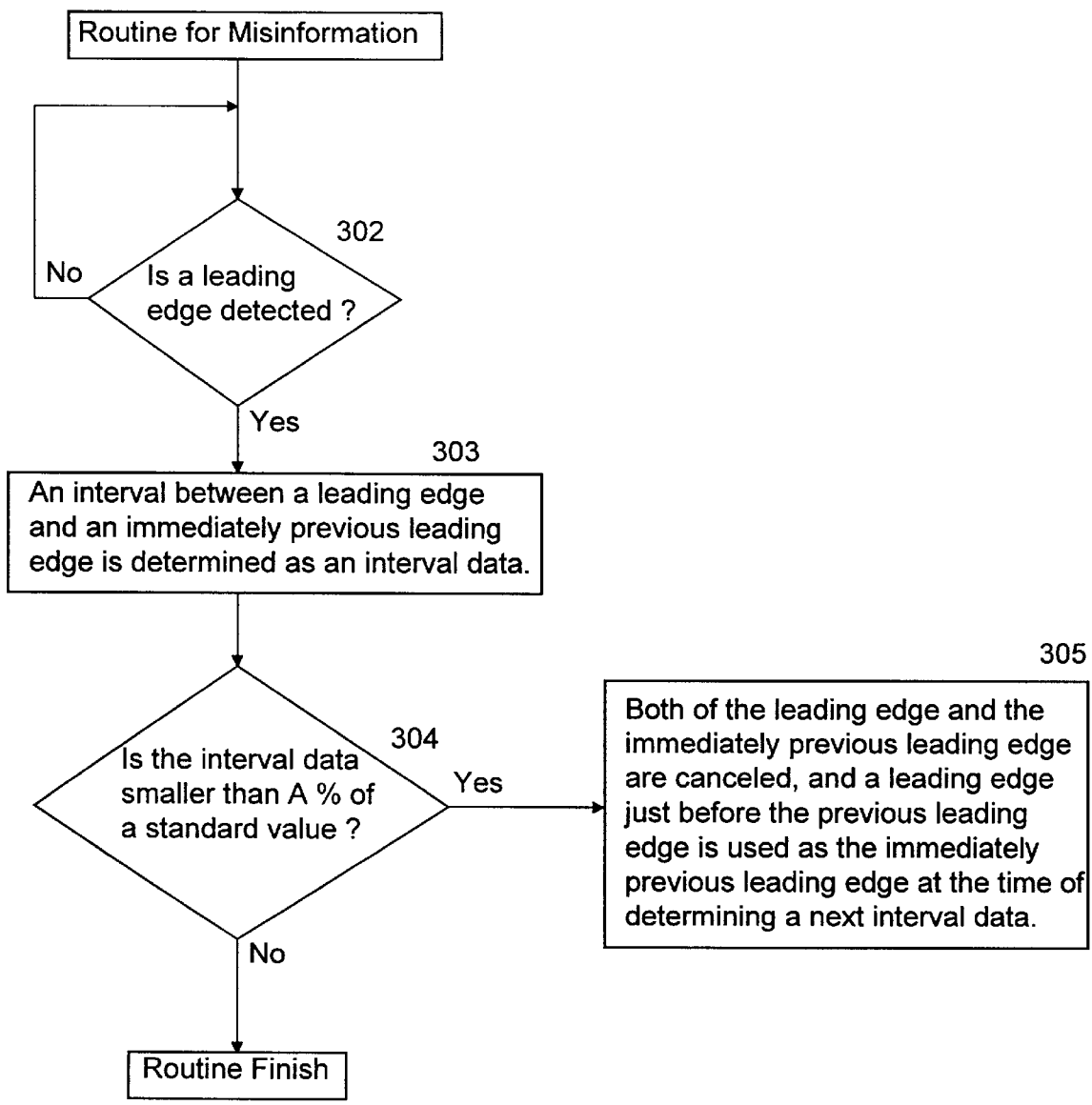
FIG. 15 is a flow chart showing a data treatment in a first heartbeat-signal revising section.

As to a misinformation including a noise (ER1) in detected heartbeat signals, as shown in FIG. 14B, the first heartbeat-signal revising section revises the heartbeat signals according to the following method, as shown in FIG. 15. That is, a leading edge of each of the heartbeat signals is detected at the step 302. At the step 303, an interval between a leading edge of a heartbeat signal and a leading edge of an immediately previous heartbeat signal is determined as an interval data. At the step 304, when the interval data is less that A % of the heartbeat-signal standard value, it is regarded as unusual, and both of the heartbeat signal (ER1) and the immediately previous heartbeat signal (En-1) are canceled. In addition, a heartbeat signal (En-2) detected immediately before the heartbeat signal (En-1) is used as an immediately previous heartbeat signal at the time of determining a next interval data (step 305). The reason for canceling both of the heartbeat signals (ER1) and (En-1) at the step 305 is explained below. The heartbeat signal (En-1) detected immediately before the abnormal heartbeat signal (ER1) is not regarded as unusual, however, there is a possibility that a small shift of the heartbeat interval appears in the heartbeat signal (En-1) as a sign of the unusual heartbeat signal. Therefore, the heartbeat signal (En-1) is canceled at the step 305 to improve the confidence of the interval data. The heartbeat signal regarded as normal at the step 304 is used to control the massage action of the applicator.

Figure 14C:
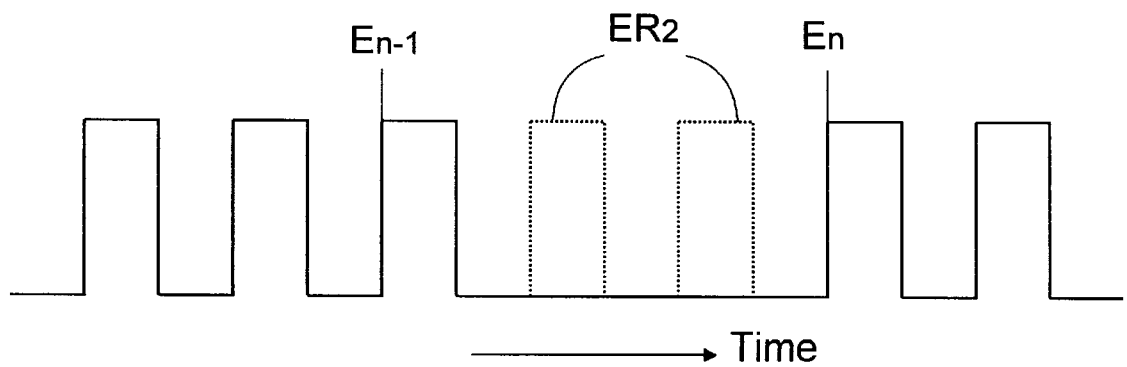
FIG. 14C is a diagram showing heartbeat signals with a loss of two heartbeat signals (a loss of information)
Figure 16:
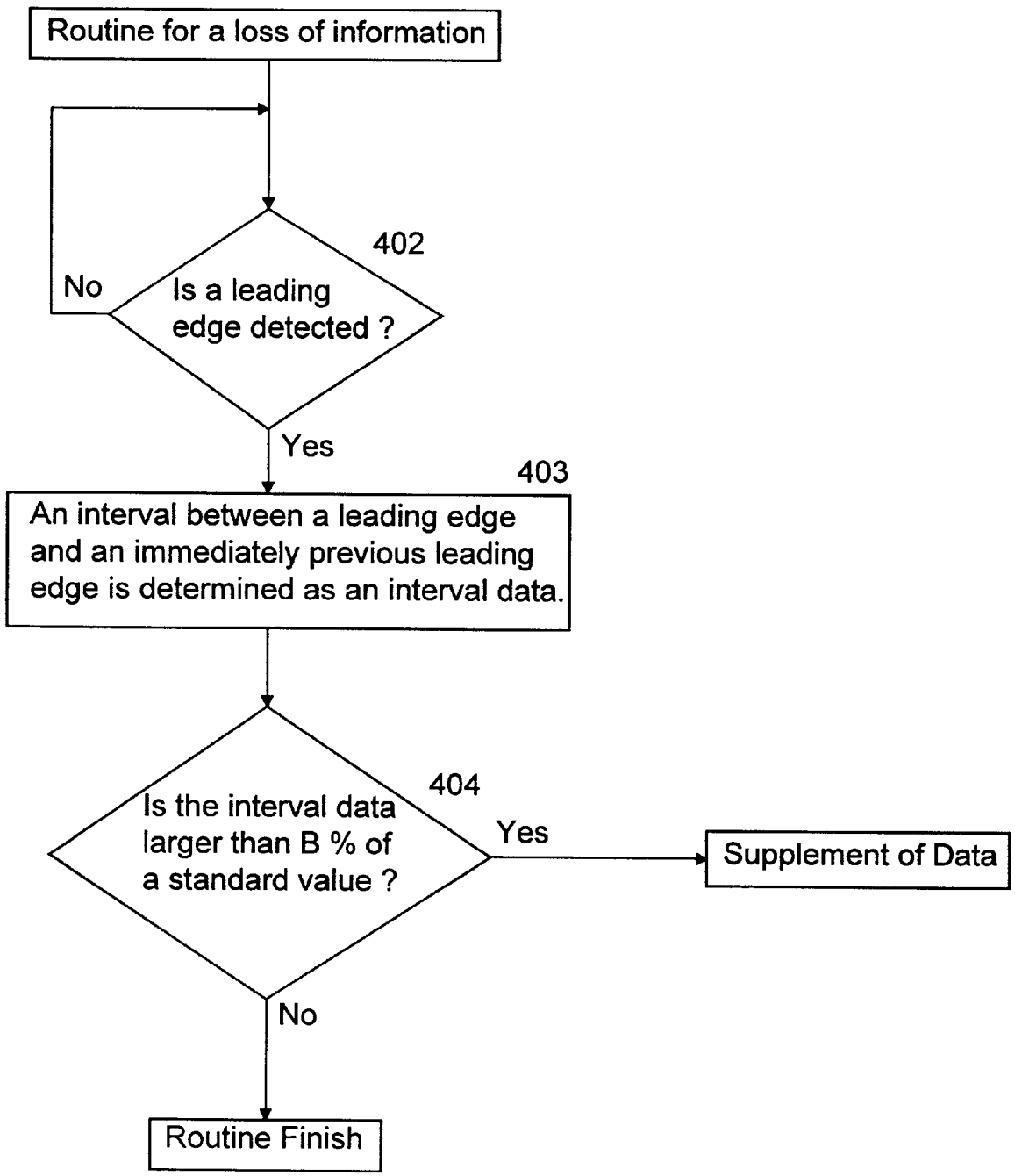
FIG. 16 is a flow chart showing a data treatment in a second heartbeat-signal revising section.
Figure 17:
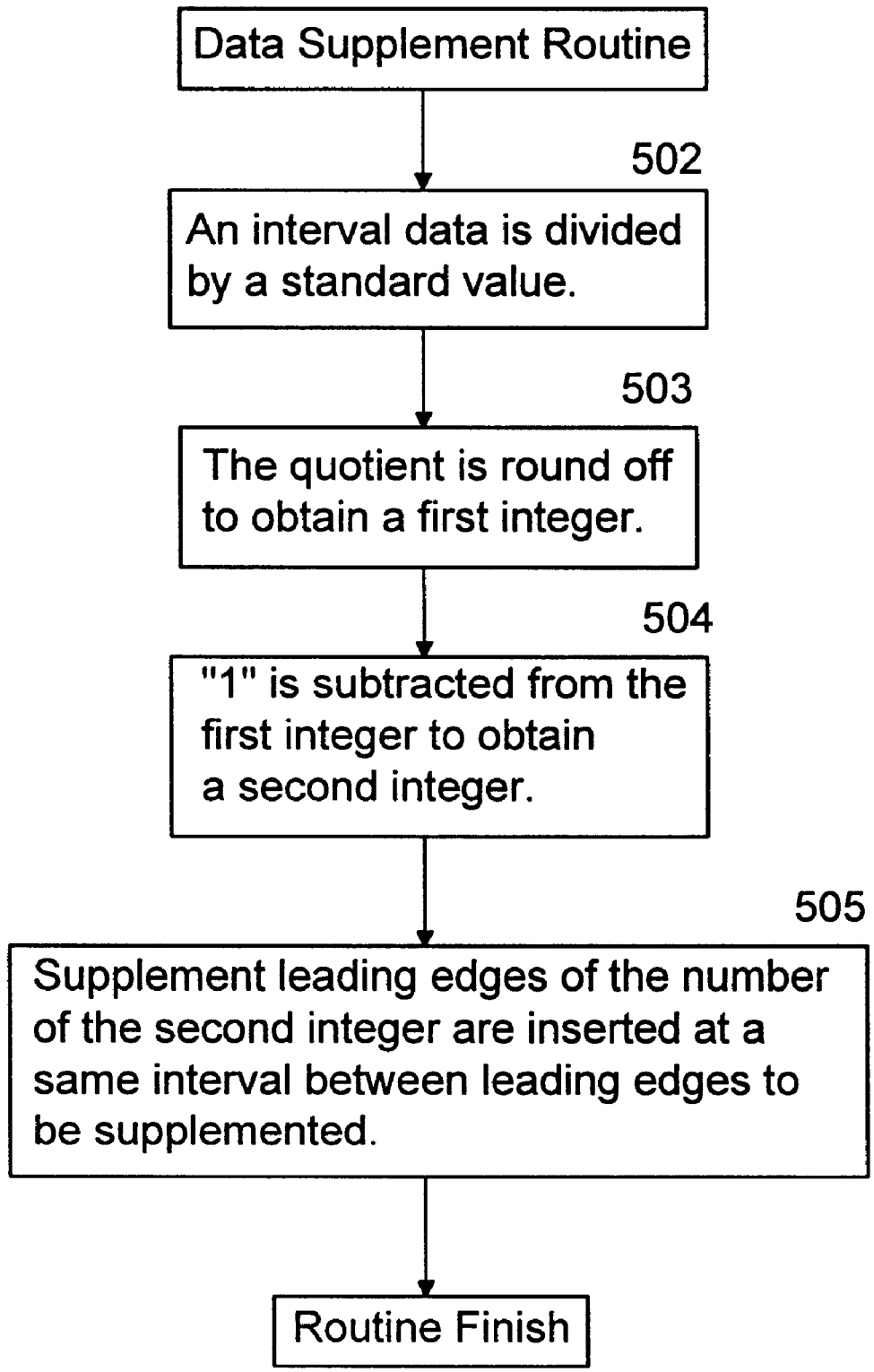
FIG. 17 is a flow chart showing a supplement procedure of heartbeat signals.

When a loss of heartbeat signals occurs between heartbeat signals (En) and (En-1), as shown in FIG. 14C, the second heartbeat number revising section revises the heartbeat signals according to the following method, as shown in FIG. 16. That is, a leading edge of each of the heartbeat signals is detected at the step 402. At the step 403, an interval between a leading edge (En) of a heartbeat signal and a leading edge of an immediately previous heartbeat signal is determined as an interval data. At the step 404, when the interval data is more than B % of the heartbeat-signal standard value, it is regarded as unusual, so that a predetermined number of heartbeat signals are supplemented between the heartbeat signals (En) and (En-1). That is, an abnormally large interval data, which allows to suppose that a plurality of heartbeat signals (ER2 shown in FIG. 14C) are lost between the heartbeat signals (En) and (En-1), is divided by the heartbeat-signal standard value (step 502). Subsequently, the quotient of the interval data divided by the standard value is rounded off to obtain a first integer at the step 503. In addition, "1" is subtracted from the first integer at the step 504 to obtain a second integer. The second integer means the number of supplement heartbeat signals to be inserted between the heartbeat signals (En) and (En-1). In FIG. 14C, the number of supplement heartbeat signals is 2. Therefore, the supplement heartbeat signals of the number of the second integer are inserted at a same interval within the abnormal interval data (step 505). The heartbeat signal regarded as normal at the step 404 is used to control the massage action of the applicator.

There is no limitation as to the threshold values A and B used in the first and second heartbeat-signal revising sections. However, it is preferred that the threshold values A and B are determined within a range of 80% to 60%, and a range of 125% to 150%, respectively. In case of providing a massage system of gradually extending the heartbeat interval (or providing a relax state such as a sleeping state), it is preferred to use a relatively large value within the above range as the threshold value B, and a relatively small value within the above range as the threshold value A. Consequently, it is possible to perform accurate revising operations of the heartbeat signals.

Figure 18:
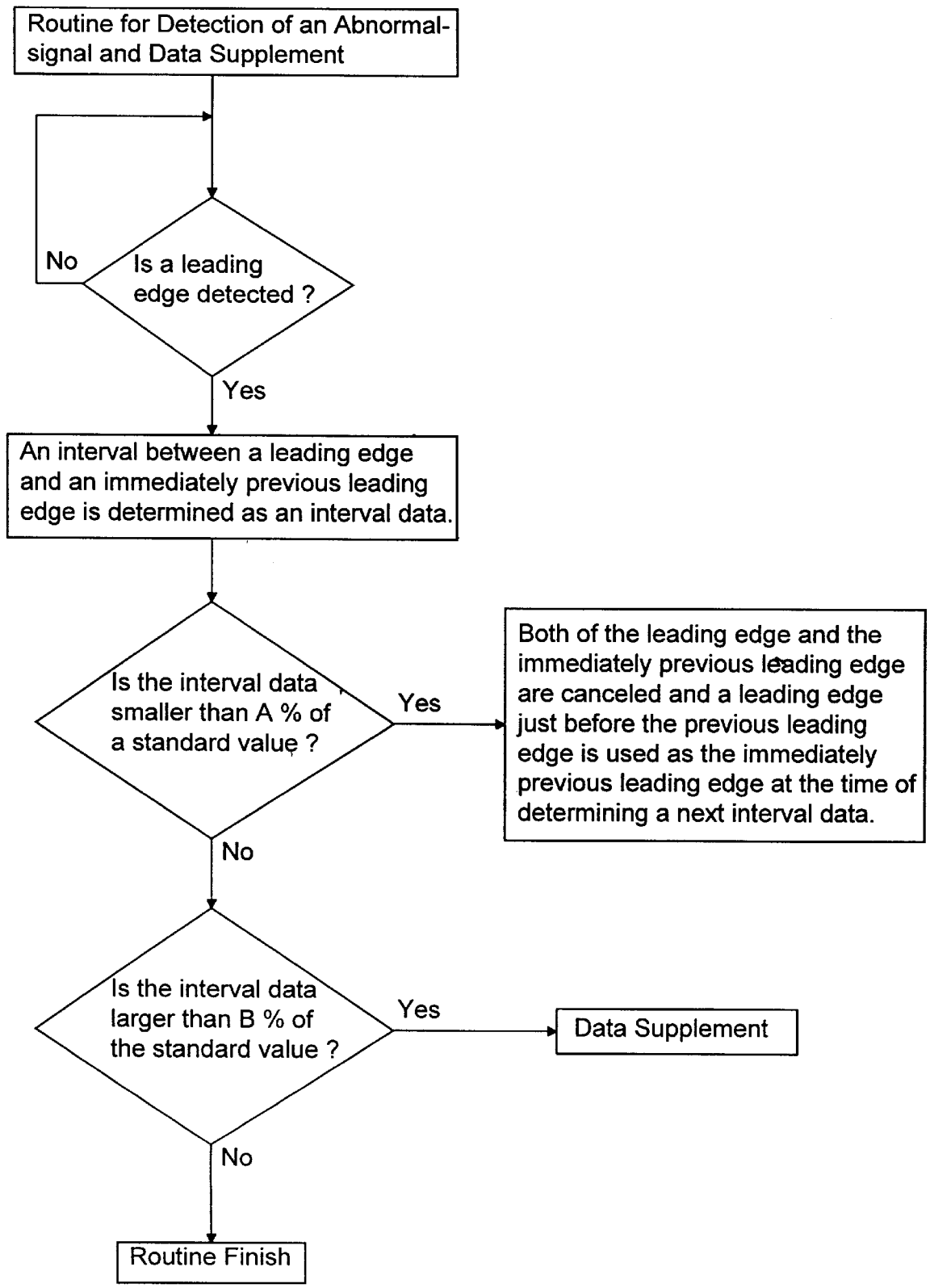
FIG 18 is a flow chart showing a procedure of revising a misinformation of a heartbeat signal and also revising a loss of heartbeat signals.

FIG. 18 shows a flow chart of a heartbeat-signal revising system, in which revising operations for a misinformation and a loss of heartbeat signals are continuously performed. This provides a simplification of algorithm and a speed-up of the revising operations.

The above-explained system performs the revising operations on a real-time basis, however, the revising operations may be performed on a batch basis, if necessary.

What is claimed is:

1. A relax inducing device comprising:

heartbeat information detecting means for successively measuring a heartbeat attainment time, which is defined as a time period necessary to count a predetermined heartbeat number, said heartbeat attainment time being measured every cycle of the predetermined heartbeat number;

change-rate determining means for determining a change rate which is defined as a ratio of an initial heartbeat attainment time measured at an initial cycle of the predetermined heartbeat number by said heartbeat information detecting means to said heartbeat attainment time measured at a subsequent cycle thereof;

stimulus loading means for providing a stimulus to the user;

relax-level determining means for determining a relax level of the user by comparing said change rate with at least one predetermined relax-level threshold value; and stimulus control means for controlling an amount of said stimulus according to said relax level determined by said relax-level determining means to induce the user into a relax state.

2. The device as set forth in claim 1, wherein said at least one relax-level threshold value is a plurality of relax-level threshold values for a multigrade evaluation of said relax level.

3. The device as set forth in claim 2, wherein said relax-level threshold values are 4% and 11% of a change rate of a heartbeat attainment time, said change rate being defined as a ratio of an initial heartbeat attainment time measured at an initial cycle of a predetermined heartbeat number to a subsequent heartbeat attainment time measured at a subsequent cycle of the predetermined heartbeat number, and said heartbeat attainment time being defined as a time period necessary to count the predetermined heartbeat number, and wherein said relax-level determining means determines said relax level from three grades of a first relax level within a range of less than 4% of said change rate, a second relax level within a range of 4% to less than 11% of said change rate, and a third relax level within a range of 11% or more of said change rate.

4. The device as set forth in claim 3, wherein said stimulus control means controls said stimulus amount such that as said relax level increases from said first relax level toward said third relax level, said stimulus amount decreases.

5. The device as set forth in claim 2, wherein said stimulus control means controls said stimulus amount such that said stimulus loading means provides a different number of stimulus per minute according to said relax level of the user.

6. The device as set forth in claim 2, wherein said stimulus control means controls said stimulus amount such that said stimulus loading means provides a different strength of stimulus according to said relax level of the user.

7. The device as set forth in claim 2, wherein said stimulus control means controls said stimulus amount such that said stimulus loading means provides a different strength of stimulus at a different number of stimulus per minute according to said relax level of the user.

8. The device as set forth in claim 1, wherein said stimulus loading means provides a kneading massage.

9. The device as set forth in claim 1, wherein said stimulus control means controls said stimulus amount to decrease a stimulus number of the massage actions provided by said stimulus loading means per minute when said said change rate provided from said change-rate determining means is constant over a predetermined period.

10. A relax inducing device comprising:
heartbeat-information detecting means for successively counting a heartbeat number every cycle of a predetermined time period;
change-rate determining means for determining a change rate ($\Delta HR$) defined by the following equation:

$$\Delta HR = 100 \times (HR(0) - HR(n))/HR(0),$$

wherein "HR(0)" is an initial heartbeat number counted by said heartbeat information detecting means at an initial cycle of the predetermined time period, and "HR(n)" is a heartbeat number counted at a subsequent cycle "n"(=1,2,3 . . . );
stimulus loading means for providing a stimulus to the user;
relax-level determining means for determining a relax level of the user by comparing said change rate provided from said change-rate determining means with at least one predetermined relax-level threshold value; and stimulus control means for controlling an amount of said stimulus according to said relax level provided from said relax-level determining means to induce the user into a relax state.

11. The device as set forth in claim 9, wherein said relax-level threshold values are 0%, 2%, 4%, 8%, 11% and 13% of said change rate of the heartbeat number, and said change rate being calculated by the equation defined in claim 5, and wherein said relax-level determining means determines said relax level from six grades of a first relax level within a range of 0% to less than 2% of said change rate, a second relax level within a rage of 2% to less than 4% of said change rate, a third relax level within a range of 4% to less than 8% of said change rate, a fourth relax level within a range of 8% to less than 11%, a fifth relax level within a range of 11% to less than 13% of said change rate, and a sixth relax level within a range of 13% or more of said change rate.

12. The device as set forth in claim 11, wherein said stimulus control means controls said stimulus amount such that as said relax level increases from said first relax level toward said sixth relax level, said stimulus amount decreases.

13. The device as set forth in claim 5, wherein said at least one relax-level threshold value is a plurality of relax-level threshold values for a multigrade evaluation of said relax level.

14. The device as set forth in claim 5, wherein said stimulus control means controls said stimulus amount such that as said heartbeat number decreases, said stimulus amount is smaller.

15. The device as set forth in claim 5, further comprising:
standard value deriving means for providing a heartbeat-signal standard value which is defined as an average value of heartbeat-signal intervals of a predetermined number of continuous heartbeat signals, said heartbeat-signal intervals having a dispersion within a required percentage; and
heartbeat-signal revising means for canceling an abnormal heartbeat signal appeared within a first interval of less than a predetermined percentage of said heartbeat-signal standard value.

16. The device as set forth in claim 5, further comprising;
standard value deriving means for providing a heartbeat-signal standard value which is defined as an average value of heartbeat-signal intervals of a predetermined number of continuous heartbeat signals, said heartbeat-signal intervals having a dispersion within a required percentage; and
heartbeat-signal revising means for inserting a supplement signal into a second interval of more than a predetermined percentage of said heartbeat-signal standard value.

17. The device as set forth in claim 16, wherein said heartbeat-signal revising means providing a required number of supplement signals at an interval substantially equal to said heartbeat-signal standard value.

18. The device as set forth in claim 5, further comprising:
standard value deriving means for providing a heartbeat-signal standard value which is defined as an average value of heartbeat-signal intervals of a predetermined number of continuous heartbeat signals said heartbeat-signal intervals having a dispersion within a required percentage; and
first heartbeat-signal revising means for canceling an abnormal heartbeat signal appeared within a first interval of less than a predetermined percentage of said heartbeat-signal standard value; and second heartbeat-signal revising means for inserting a supplement signal into a second interval of more than a predetermined percentage of said heartbeat-signal standard value.

19. A relax inducing device comprising:

heartbeat information detecting means for successively measuring a heartbeat attainment time, which is defined as a time period necessary to count a predetermined heartbeat number, said heartbeat attainment time being measured every cycle of the predetermined heartbeat number;

a change-rate determining means for determining a change rate ($\Delta T$) defined by the following equation:

$$\Delta T = 100 \times (T(0) - T(n))/T(0),$$

wherein "T(0)" is an initial heartbeat attainment time measured at an initial cycle of the predetermined heartbeat number by said heartbeat information detecting means, and "T(n)" is a heartbeat attainment time measured at a subsequent cycle "n" (=1,2,3 . . . );

stimulus loading means for providing a stimulus to the user;

relax-level determining means for determining a relax level of the user by comparing said change rate provided from said change-rate determining means with at least one predetermined relax-level threshold value; and stimulus control means for controlling an amount of stimulus according to said relax level provided from said relax-level determining means to induce the user into a relax state.

* * * * *

UNITED STATES PATENT AND TRADEMARK OFFICE
CERTIFICATE OF CORRECTION

PATENT NO.: 5,993,401
DATED : November 30, 1999
INVENTOR(S): INBE et al.

It is certified that an error appears in the above-identified patent and that said Letters Patent is hereby corrected as shown below:

On the title page of the patent in item [87], change "PCT Pub Date: March 7, 1997" to be --PCT Pub. Date: July 3, 1997--.

Signed and Sealed this

Twelfth Day of September, 2000

Attest:

Q. TODD DICKINSON

*Attesting Officer*          *Director of Patents and Trademarks*